US008465753B2

(12) United States Patent
Greenstein

(10) Patent No.: US 8,465,753 B2
(45) Date of Patent: Jun. 18, 2013

(54) **COMBINATION VACCINES AGAINST *MYCOBACTERIUM* SP. AND METHODS OF USING THE SAME**

(76) Inventor: Robert J. Greenstein, Tenafly, NJ (US)

( * ) Notice: Subject to any disclaimer, the term of this patent is extended or adjusted under 35 U.S.C. 154(b) by 148 days.

(21) Appl. No.: 12/956,064

(22) Filed: Nov. 30, 2010

(65) Prior Publication Data

US 2011/0070261 A1 Mar. 24, 2011

Related U.S. Application Data

(63) Continuation-in-part of application No. 12/108,144, filed on Apr. 23, 2008, now Pat. No. 7,846,420.

(60) Provisional application No. 60/913,315, filed on Apr. 23, 2007.

(51) Int. Cl.
*A61K 39/04* (2006.01)
*A61K 49/00* (2006.01)
*A61K 45/00* (2006.01)

(52) U.S. Cl.
USPC ....... 424/248.1; 424/9.1; 424/9.2; 424/234.1; 424/278.1; 435/41; 435/69.1; 435/243; 435/253.1

(58) Field of Classification Search
USPC .................. 424/9.1, 9.2, 184.1, 234.1, 248.1, 424/278.1; 435/41, 69.1, 243, 253.1
See application file for complete search history.

(56) References Cited

U.S. PATENT DOCUMENTS

| | | | |
|---|---|---|---|
| 6,156,322 A | 12/2000 | Hermon-Taylor et al. | 424/248.1 |
| 7,311,922 B1 | 12/2007 | Skeiky et al. | 424/248.1 |
| 7,579,141 B2 | 8/2009 | Gennaro | 435/4 |
| 7,670,609 B2 | 3/2010 | Shafferman et al. | 424/248.1 |
| 7,722,861 B2 | 5/2010 | Jacobs et al. | 424/93.2 |
| 7,745,141 B2 | 6/2010 | Laal et al. | 435/7.1 |
| 2003/0044431 A1* | 3/2003 | Schurig et al. | 424/252.1 |
| 2004/0234533 A1* | 11/2004 | Aldwell et al. | 424/184.1 |
| 2004/0260078 A1 | 12/2004 | Hermon-Taylor et al. | 536/23.1 |
| 2006/0204521 A1 | 9/2006 | Hermon-Taylor et al. | 424/200.1 |

OTHER PUBLICATIONS

Romano, M. et al. Expert Reviews of Vaccines, vol. 8, issue 9, pp. 1237-1256, 2009.*
Anderson et al. "Proteins Released from *Mycobacterium tuberculosis* During Growth" Infection and Immunity 1991 vol. 59(6):1905-1910.
Autschbach et al. "High Prevalence of *Mycobacterium avium* Subspecies *paratuberculosis* IS900 DNA in Gut Tissues from Individuals with Crohn's Disease" Gut 2005 vol. 54:944-949.
Borody et al. "Treatment of Severe Crohn's Disease Using Antimycobacterial Triple Therapy—Approaching a Cure?" Digest Liver Dis 2002 vol. 34:29-38.
Cameron et al. "Identification and Characterization of a Putative Serine Protease Expressed in vivo by *Mycobacterium avium* subsp. *paratuberculosis*" Microbiology 1994 vol. 140:1977-1982.
De Kesel et al. "Cloning and Expression of Portions of the 34-Kilodalton-Protein Gene of *Mycobacterium paratuberculosis*: Its Application to Serological Analysis of Johne's Disease" Journal of Clinical Microbiology 1993 vol. 31(4):947-954.
De Kesel et al. "Composition and Immunological Properties of the Protein Fraction of A36, a Major Antigen Complex of *Mycobacterium paratuberculosis*" Scandinavian Journal of Immunology 1992 vol. 36:201-212.
Dietrich et al. "Synergistic Effect of *Bacillus* Calmette Guerin and a *Tuberculosis* Subunit Vaccine in Cationic Liposomes: Increase Immunogenicity and Protection" Journal of Immunology 2007 vol. 178:3721-3730.
El-Zaatari et al. "Characterization of a Specific *Mycobacterium parartuberculosis* Recombinant Clone Expressing 35,000-Molecular-Weight Antigen and Reactivity with Sera from Animals with Clinical and Subclinical Johne's Disease" Journal of Clinical Microbiology 1997 vol. 35(7):1794-1799.
El-Zaatari et al. "Identification and Characterization of *Mycobacterium paratuberculosis* Recombinant Proteins Expressed in *E. coli*" Current Microbiology 1994 vol. 29:177-184.
El-Zaatari et al. "Nucleotide Sequence Analysis and Seroreactivities of the 65K Heat Shock Protein from *Mycobacterium paratuberculosis*" Clinical and Diagnostic Laboratory Immunology 1995 vol. 2(6):657-664.
Gilberts et al. "Molecular Evidence for Two Forms of Crohn Disease" Proc. Natl. Acad. Sci. USA 1994 vol. 91:12721-12724.
Gilot et al. "Isolation and Sequencing of the Gene Coding for an Antigenic 34-Kilodalton Protein of *Mycobacterium paratuberculosis*" Journal of Bacteriology 1993 vol. 175(15):4930-4935.
Greenstein, R.J. and Collins, M.T. "Emerging Pathogens: Is *Mycobacterium avium* Subspecies *paratuberculosis* Zoonotic?" Lancet 2004 vol. 364:396-397.
Greenstein, R.J. "Does the 'I' in IBD Stand for Infectious Bowel Disease and Is the Causative Organism *Mycobacterium avium* Subspecies *paratuberculosis* (MAP)? A Unifying Hypothesis" Annals of the New York Academy of Sciences, Inflammatory Bowel Disease, Genetics, Barrier Function, Immunologic & Microbial Pathways 2006 vol. 1072:24.
Greenstein, R.J. "Is Crohn's Disease Caused by a Mycobacterium? Comparison with Leprosy, *Tuberculosis*, and Johne's Disease" The Lancet Infectious Diseases 2003 vol. 3:507-514.
Greenstein et al. "Perforating and Non-perforating Indications for Repeated Operations in Crohn's Disease: Evidence for Two Clinical Forms" Gut 1988 vol. 29:588-592.
Greenstein, R.J. "Towards Curing Inflammatory Bowel Disease (IBD): Lessons from other Mycobacterioses" Crohn's and Colitis Foundation (CCFA) National Research and Clinical Conference, Fourth Annual Advances in Inflammatory Bowel Disease, Miami, FL 2005:211.
Greenstein, R.J. "Was a Causative Relation Between Crohn's Disease (CD) and *Mycobacterium avium* subspecies *paratuberculosis* (MAP) Missed, in Part, by Studying the Wrong Antibiotics?" Annals of the New York Academy of Sciences, Inflammatory Bowel Disease, Genetics, Barrier Function Immunologic and Microbial Pathways 2006 vol. 1072:25.

(Continued)

*Primary Examiner* — Rodney P. Swartz
(74) *Attorney, Agent, or Firm* — Licata & Tyrrell P.C.

(57) ABSTRACT

The invention relates to a combination vaccine against *Mycobacterium avium* subspecies *paratuberculosis* (MAP) and *M. tuberculosis* and/or *M. bovis* for use in methods of immunizing a subject against mycobacterial infection, preventing or treating mycobacterial infection, and preventing a disease associated with mycobacterial infection.

11 Claims, No Drawings

OTHER PUBLICATIONS

Hermon-Taylor, J. "The Causation of Crohn's Disease and Treatment with Antimocrobial Drugs" Ital. J. Gastroenterol Hepatol 1998 vol. 30:607-610.

Hines et al. "Effects of Vaccination on Johne's Disease AGID and ELISA Tests in Experimentally Challenged Baby Goats" 8th International Colloquium on *Paratuberculosis*, Copenhagen, Denmark 2005 Theme 5:105.

Hines et al. "Efficacy of Spheroplastic and Cell Wall Competent Vaccines for Johne's Disease in Experimentally Challenged Baby Goats" 8th International Colloquium on *Paratuberculosis*, Copenhagen, Denmark 2005 Theme 3a:54.

Naser et al. "Culture of *Mycobacterium avium* Subspecies *paratuberculosis* from the Blood of Patients with Crohn's Disease" Lancet 2004 vol. 364:1039-1044.

Olsen et al. "Alkyl Hydroperoxide Reductases C and D are Major Antigens Constitutively Expressed by *Mycobacterium avium* subsp. *paratuberculosis*" Infection and Immunology 2000 vol. 68(2):801-808.

Shinnick, T.M. "The 65-Kilodalton Antigen of *Mycobacterium tuberculosis*" Journal of Bacteriology 1987 vol. 169(3):1080-1088.

Silbaq et al. "Characterization of a 34-Kilodalton Protein of *Mycobacterium leprae* That is Isologous to the Immunodominant 34-Kilodalton Antigen of *Mycobacterium paratuberculosis*" Infection and Immunity 1998 vol. 66(11):5576-5579.

Thole et al. "Characterization, Sequence Determination, and Immunogenicity of a 64-Kilodalton Protein of *Mycoboterium bovis* BCG Expressed in *Escherichia coli* K-12" Infection and Immunity 1987 vol. 55(6):1466-1475.

Thole et al. "Use of Recombinant Antigens Expressed in *Escherichia coli* K-12 to Map B-Cell and T-Cell Epitopes on the Immunodominant 65-Kilodalton Protein of *Mycobacerium bovis* BCG" Infection and Immunity 1988 vol. 56(6):1633-1640.

Uzonna et al. "Oral Vaccination for *Paratuberculosis* in calves" 7th International Colloquium on *Paratuberculosis* 2002 Section 2:41.

* cited by examiner

SEQUENCE LISTING

<160> NUMBER OF SEQ ID NOS: 7

<210> SEQ ID NO 1

```
<211> LENGTH: 100
<212> TYPE: PRT
<213> ORGANISM: Mycobacterium avium subsp. paratuberculosis

<400> SEQUENCE: 1

Met Ala Lys Val Asn Ile Lys Pro Leu Glu Asp Lys Ile Leu Val Gln
1               5                   10                  15

Ala Asn Glu Ala Glu Thr Thr Thr Ala Ser Gly Leu Val Ile Pro Asp
            20                  25                  30

Thr Ala Lys Glu Lys Pro Gln Glu Gly Thr Val Val Ala Val Gly Pro
        35                  40                  45

Gly Arg Trp Asp Asp Gly Ala Lys Arg Ile Pro Leu Asp Val Ser
    50                  55                  60

Glu Gly Asp Thr Val Ile Tyr Ser Lys Tyr Gly Gly Thr Glu Ile Lys
65                  70                  75                  80

Tyr Asn Gly Glu Glu Tyr Leu Ile Leu Ser Ala Arg Asp Val Leu Ala
                85                  90                  95

Val Val Ser Lys
            100

<210> SEQ ID NO 2
<211> LENGTH: 178
<212> TYPE: PRT
<213> ORGANISM: Mycobacterium avium subsp. paratuberculosis

<400> SEQUENCE: 2

Met Ser Val Glu Asn Leu Lys Glu Ala Leu Pro Glu Tyr Ala Lys Asp
1               5                   10                  15

Leu Lys Leu Asn Leu Gly Ser Ile Thr Arg Thr Thr Glu Leu Asn Glu
            20                  25                  30

Glu Gln Leu Trp Gly Thr Leu Leu Ala Ser Ala Ala Thr Arg Asn
        35                  40                  45

Thr Gln Val Leu Thr Glu Ile Gly Ala Glu Ala Ala Asp Thr Leu Ser
    50                  55                  60

Ala Glu Ala Tyr His Ala Ala Leu Gly Ala Ala Ser Val Met Ala Met
65                  70                  75                  80

Asn Asn Val Phe Tyr Arg Gly Arg Gly Phe Leu Asp Gly Lys Tyr Asp
                85                  90                  95

Asp Leu Arg Ala Gly Leu Arg Met Asn Ile Ile Gly Asn Pro Gly Val
            100                 105                 110

Glu Lys Ala Asn Phe Glu Leu Trp Cys Phe Ala Val Ser Ala Ile Asn
        115                 120                 125

Gly Cys Pro Asp Cys Val Ala Ser His Glu His Thr Leu Arg Glu Ala
    130                 135                 140

Gly Val Ser Arg Glu Thr Ile Gln Glu Ala Leu Lys Ala Ala Ile
145                 150                 155                 160

Ile Ser Gly Val Ala Gln Ala Ile Val Ala Ser Gln Thr Leu Ala Thr
                165                 170                 175

Ala Gly

<210> SEQ ID NO 3
<211> LENGTH: 298
<212> TYPE: PRT
<213> ORGANISM: Mycobacterium avium subsp. paratuberculosis

<400> SEQUENCE: 3

Met Thr Tyr Ser Pro Gly Ser Pro Gly Tyr Pro Pro Ala Gln Ser Gly
1               5                   10                  15
```

```
Gly Thr Tyr Ala Gly Ala Thr Pro Ser Phe Ala Lys Asp Asp Gly
                20                  25                  30

Lys Ser Lys Leu Pro Leu Tyr Leu Asn Ile Ala Val Val Ala Leu Gly
        35                  40                  45

Phe Ala Ala Tyr Leu Leu Asn Phe Gly Pro Thr Phe Thr Ile Gly Ala
 50                  55                  60

Asp Leu Gly Pro Gly Ile Gly Gly Arg Ala Gly Asp Ala Gly Thr Ala
 65                  70                  75                  80

Val Val Val Ala Leu Leu Ala Ala Leu Leu Ala Gly Leu Gly Leu Leu
                85                  90                  95

Pro Lys Ala Lys Ser Tyr Val Gly Val Val Ala Val Val Ala Val Leu
            100                 105                 110

Ala Ala Leu Leu Ala Ile Thr Glu Thr Ile Asn Leu Pro Ala Gly Phe
            115                 120                 125

Ala Ile Gly Trp Ala Met Trp Pro Leu Val Ala Cys Val Val Leu Gln
        130                 135                 140

Ala Ile Ala Ala Val Val Val Leu Leu Asp Ala Gly Val Ile Thr
145                 150                 155                 160

Ala Pro Ala Pro Arg Pro Lys Tyr Asp Pro Tyr Ala Gln Tyr Gly Gln
                165                 170                 175

Tyr Gly Gln Tyr Gly Gln Tyr Gly Gln Gln Pro Tyr Tyr Gly Gln Pro
            180                 185                 190

Gly Gly Gln Pro Gly Gly Gln Pro Gly Gly Gln Gln His Ser Pro Gln
        195                 200                 205

Gly Tyr Gly Ser Gln Tyr Gly Gly Tyr Gly Gln Gly Gly Ala Pro Thr
    210                 215                 220

Gly Gly Phe Gly Ala Gln Pro Ser Pro Gln Ser Gly Pro Gln Gln Ser
225                 230                 235                 240

Ala Gln Gln Gln Gly Pro Ser Thr Pro Thr Gly Phe Pro Ser Phe
                245                 250                 255

Ser Pro Pro Pro Asn Val Gly Gly Ser Asp Ser Gly Ser Ala Thr
            260                 265                 270

Ala Asn Tyr Ser Glu Gln Ala Gly Gln Gln Ser Tyr Gly Gln Glu
        275                 280                 285

Pro Ser Ser Pro Ser Gly Pro Thr Pro Ala
    290                 295

<210> SEQ ID NO 4
<211> LENGTH: 361
<212> TYPE: PRT
<213> ORGANISM: Mycobacterium avium subsp. paratuberculosis

<400> SEQUENCE: 4

Met Ser Lys Ser His His His Arg Ser Val Trp Trp Ser Trp Leu Val
1               5                   10                  15

Gly Val Leu Thr Val Val Gly Leu Gly Leu Gly Leu Gly Ser Gly Val
                20                  25                  30

Gly Leu Ala Pro Ala Ser Ala Ala Pro Ser Gly Leu Ala Leu Asp Arg
            35                  40                  45

Phe Ala Asp Arg Pro Leu Ala Pro Ile Asp Pro Ser Ala Met Val Gly
 50                  55                  60

Gln Val Gly Pro Gln Val Val Asn Ile Asp Thr Lys Phe Gly Tyr Asn
65                  70                  75                  80

Asn Ala Val Gly Ala Gly Thr Gly Ile Val Ile Asp Pro Asn Gly Val
                85                  90                  95
```

```
Val Leu Thr Asn Asn His Val Ile Ser Gly Ala Thr Glu Ile Ser Ala
            100                 105                 110

Phe Asp Val Gly Asn Gly Gln Thr Tyr Ala Val Asp Val Gly Tyr
        115                 120                 125

Asp Arg Thr Gln Asp Ile Ala Val Leu Gln Leu Arg Gly Ala Ala Gly
        130                 135                 140

Leu Pro Thr Ala Thr Ile Gly Gly Glu Ala Thr Val Gly Glu Pro Ile
145                 150                 155                 160

Val Ala Leu Gly Asn Val Gly Gly Gln Gly Gly Thr Pro Asn Ala Val
                165                 170                 175

Ala Gly Lys Val Val Ala Leu Asn Gln Ser Val Ser Ala Thr Asp Thr
            180                 185                 190

Leu Thr Gly Ala Gln Glu Asn Leu Gly Gly Leu Ile Gln Ala Asp Ala
        195                 200                 205

Pro Ile Lys Pro Gly Asp Ser Gly Gly Pro Met Val Asn Ser Ala Gly
        210                 215                 220

Gln Val Ile Gly Val Asp Thr Ala Ala Thr Asp Ser Tyr Lys Met Ser
225                 230                 235                 240

Gly Gly Gln Gly Phe Ala Ile Pro Ile Gly Arg Ala Met Ala Val Ala
                245                 250                 255

Asn Gln Ile Arg Ser Gly Ala Gly Ser Asn Thr Val His Ile Gly Pro
            260                 265                 270

Thr Ala Phe Leu Gly Leu Gly Val Thr Asp Asn Asn Gly Asn Gly Ala
        275                 280                 285

Arg Val Gln Arg Val Val Asn Thr Gly Pro Ala Ala Ala Gly Ile
        290                 295                 300

Ala Pro Gly Asp Val Ile Thr Gly Val Asp Thr Val Pro Ile Asn Gly
305                 310                 315                 320

Ala Thr Ser Met Thr Glu Val Leu Val Pro His His Pro Gly Asp Thr
                325                 330                 335

Ile Ala Val His Phe Arg Ser Val Asp Gly Gly Glu Arg Thr Ala Asn
            340                 345                 350

Ile Thr Leu Ala Glu Gly Pro Pro Ala
        355                 360

<210> SEQ ID NO 5
<211> LENGTH: 319
<212> TYPE: PRT
<213> ORGANISM: Mycobacterium avium subsp. paratuberculosis
<220> FEATURE:
<221> NAME/KEY: misc_feature
<222> LOCATION: (67)..(67)
<223> OTHER INFORMATION: Xaa can be any naturally occurring amino acid

<400> SEQUENCE: 5

Met Pro Ser Ala Ala Ser Thr Ser Ala Ala Pro Pro Ser His Arg Ala
1               5                   10                  15

Ala Leu Ser Ala Ala Ala Gly Pro Pro Gly Cys Trp Trp Pro Ala Ala
            20                  25                  30

Gly Arg Arg Gln Gly Glu Arg Gly Arg Val Leu Gly Leu Ala Ala
        35                  40                  45

Val Gly Gln Arg Trp Leu Ile Pro Leu Asp His Gly Ala Val Gly Val
    50                  55                  60

Gly Leu Xaa Gly Arg Lys Ala Asp Gly Val Gly Val Gly Gln Leu His
65                  70                  75                  80

Arg Gln Pro Glu Gln Gly Glu Leu Val Gly Pro Asp Ala Ala Ala Arg
```

-continued

```
                85                  90                  95
Gly Gly Ser Gln Val Thr Glu Arg Thr Val Pro Asp Ala Ala Ser Arg
            100                 105                 110
Ser Ser Arg Ala Val Gln Pro Gly Met Val Ser Val Cys Ala Ala Ala
            115                 120                 125
Thr Leu Gly Ser Ala Thr Val Ser Ala Val Val Ala Ala Pro Val Phe
        130                 135                 140
Asp Ser Leu Gly Thr Trp Lys Val Thr Thr Ala Met Ala Pro Arg Thr
145                 150                 155                 160
Gly Leu Ser Leu Pro Ala Cys Thr Cys Ala Asp Ala Ile Gly Asp Gln
                165                 170                 175
Ala Thr Asp Pro Arg His Arg Ala Ala Thr Ala Thr Ser Arg Arg Gly
            180                 185                 190
Ala Arg Arg Leu Arg Gly Gly Met Arg Val Ala Gln Pro Glu Ala Gly
            195                 200                 205
His Gln Val Arg Leu Asp Ala Val Glu Leu Arg Gly Asp Gly Gly Val
        210                 215                 220
Ser Arg Pro Ala Pro Gly Gly His Val Leu Arg Gly Gly His Arg
225                 230                 235                 240
Gly Arg Gln Val Gly Glu Pro Leu Gly Asp Gly Asp Glu Leu Leu
                245                 250                 255
Gly Leu Ala Val Leu Gly Leu Arg Ser Cys Thr Ser Arg Asn Asp Phe
            260                 265                 270
Ser Ala Pro Ala Met Arg Ala Asp Ser Trp Ala Pro Trp Pro Glu Asn
            275                 280                 285
Trp Pro Ile Trp Ala Asn Gly Thr Pro Ser Arg Ser Ala Arg Arg Trp
        290                 295                 300
Ser Ile Ser Ala Arg Ala Glu Thr Gly Arg Gly Arg Arg Thr Gly
305                 310                 315

<210> SEQ ID NO 6
<211> LENGTH: 195
<212> TYPE: PRT
<213> ORGANISM: Mycobacterium avium subsp. paratuberculosis

<400> SEQUENCE: 6

Met Pro Leu Leu Thr Ile Gly Asp Gln Phe Pro Ala Tyr Glu Leu Thr
1               5                   10                  15
Ala Leu Ile Ala Gly Asp Leu Ser Lys Val Asp Ala Lys Gln Pro Gly
            20                  25                  30
Asp Tyr Phe Thr Thr Val Thr Ser Glu Asp His Ala Gly Lys Trp Arg
        35                  40                  45
Val Val Phe Phe Trp Pro Lys Asp Phe Thr Phe Val Cys Pro Thr Glu
    50                  55                  60
Ile Ala Thr Phe Gly Lys Leu Asn Asp Glu Phe Glu Asp Arg Asp Ala
65                  70                  75                  80
Gln Val Leu Gly Val Ser Ile Asp Ser Glu Phe Val His Phe Asn Trp
                85                  90                  95
Arg Ala Gln His Glu Asp Leu Lys Asn Leu Pro Phe Pro Met Leu Ser
            100                 105                 110
Asp Ile Lys Arg Glu Leu Ser Leu Ala Thr Gly Val Leu Asn Ala Asp
            115                 120                 125
Gly Val Ala Asp Arg Ala Thr Phe Ile Val Asp Pro Asn Asn Glu Ile
        130                 135                 140
Gln Phe Val Ser Val Thr Ala Gly Ser Val Gly Arg Asn Val Glu Glu
```

```
                145                 150                 155                 160
Val Leu Arg Val Leu Asp Ala Leu Gln Ser Asp Glu Leu Cys Ala Cys
                    165                 170                 175

Asn Trp Arg Lys Gly Asp Pro Thr Leu Asn Ala Thr Glu Leu Leu Lys
                180                 185                 190

Ala Ser Ala
        195

<210> SEQ ID NO 7
<211> LENGTH: 582
<212> TYPE: PRT
<213> ORGANISM: Mycobacterium avium subsp. paratuberculosis

<400> SEQUENCE: 7

Met Leu Gly Arg Asp Gly Glu Ala Arg Leu Cys Arg Arg Pro Thr Ala
1               5                   10                  15

Ala Ala Trp Ser Ser Val Ala Gly Thr Ala Pro Gly Gln Asp Val Ser
                20                  25                  30

Ser Pro Ile Arg Arg Asn His Phe Ala Met Ala Lys Thr Ile Ala Tyr
            35                  40                  45

Asp Glu Glu Ala Arg Arg Gly Leu Glu Arg Gly Leu Asn Ala Leu Ala
        50                  55                  60

Asp Ala Val Lys Val Thr Leu Gly Pro Lys Gly Arg Asn Val Val Leu
65                  70                  75                  80

Glu Lys Lys Trp Gly Ser Pro Thr Ile Thr Asn Asp Gly Val Ser Ile
                85                  90                  95

Ala Lys Glu Ile Glu Leu Glu Asp Pro Tyr Glu Lys Ile Gly Ala Glu
                100                 105                 110

Leu Val Lys Glu Val Ala Lys Lys Thr Asp Asp Val Ala Gly Asp Gly
            115                 120                 125

Thr Thr Thr Ala Thr Val Leu Ala Gln Ala Leu Val Arg Glu Gly Leu
130                 135                 140

Arg Asn Val Ala Ala Gly Ala Asn Pro Leu Gly Leu Lys Arg Gly Ile
145                 150                 155                 160

Glu Lys Ala Val Glu Lys Val Thr Glu Thr Leu Leu Lys Ser Ala Lys
                165                 170                 175

Glu Val Glu Thr Lys Asp Gln Ile Ala Ala Thr Ala Ala Ile Ser Ala
                180                 185                 190

Gly Asp Gln Ser Ile Gly Asp Leu Ile Ala Glu Ala Met Asp Lys Val
            195                 200                 205

Gly Asn Glu Gly Val Ile Thr Val Glu Glu Ser Asn Thr Phe Gly Leu
        210                 215                 220

Gln Leu Glu Leu Thr Glu Gly Met Arg Phe Asp Lys Gly Tyr Ile Ser
225                 230                 235                 240

Gly Tyr Phe Val Thr Asp Ala Glu Arg Gln Glu Ala Val Leu Glu Asp
                245                 250                 255

Pro Phe Ile Leu Leu Val Ser Ser Lys Val Ser Thr Val Lys Asp Leu
                260                 265                 270

Leu Pro Leu Leu Glu Lys Val Ile Gln Ala Gly Lys Pro Leu Leu Ile
            275                 280                 285

Ile Ala Glu Asp Val Glu Gly Glu Ala Leu Ser Thr Leu Val Val Asn
        290                 295                 300

Lys Ile Arg Gly Thr Phe Lys Ser Val Ala Val Lys Ala Pro Gly Phe
305                 310                 315                 320

Gly Asp Arg Arg Lys Ala Met Leu Gln Asp Met Ala Ile Leu Thr Gly
```

```
                       325                 330                 335
Gly Gln Val Ile Ser Glu Glu Val Gly Leu Ser Leu Glu Ser Ala Asp
            340                 345                 350

Ile Ser Leu Leu Gly Lys Ala Arg Lys Val Val Val Thr Lys Asp Glu
            355                 360                 365

Thr Thr Ile Val Glu Gly Ala Gly Asp Ser Asp Ala Ile Ala Gly Arg
    370                 375                 380

Val Ala Gln Ile Arg Thr Glu Ile Glu Asn Ser Asp Ser Asp Tyr Asp
385                 390                 395                 400

Arg Glu Lys Leu Gln Glu Arg Leu Ala Lys Leu Ala Gly Gly Val Ala
            405                 410                 415

Val Ile Lys Ala Gly Ala Ala Thr Glu Val Glu Leu Lys Glu Arg Lys
            420                 425                 430

His Arg Ile Glu Asp Ala Val Arg Asn Ala Lys Ala Ala Val Glu Glu
            435                 440                 445

Gly Ile Val Ala Gly Gly Gly Val Ala Leu Leu His Ala Ile Pro Ala
    450                 455                 460

Leu Asp Glu Leu Lys Leu Glu Gly Glu Ala Thr Gly Ala Asn Ile
465                 470                 475                 480

Val Arg Val Ala Leu Glu Arg Pro Leu Lys Gln Ile Ala Phe Asn Gly
            485                 490                 495

Gly Leu Glu Pro Gly Val Val Ala Glu Lys Val Arg Asn Ser Pro Ala
            500                 505                 510

Gly Thr Gly Leu Asn Ala Ala Thr Gly Lys Tyr Glu Asp Leu Leu Lys
            515                 520                 525

Ala Gly Ile Thr Glu Pro Val Lys Val Thr Arg Ser Ala Leu Gln Asn
    530                 535                 540

Ala Ala Ser Ile Ser Gly Leu Phe Leu Thr Thr Glu Ala Val Val Ala
545                 550                 555                 560

Asp Lys Pro Glu Lys Thr Ala Pro Pro Ala Gly Asp Pro Thr Gly Gly
            565                 570                 575

Met Gly Gly Met Asp Phe
            580
```

COMBINATION VACCINES AGAINST *MYCOBACTERIUM* SP. AND METHODS OF USING THE SAME

INTRODUCTION

This application is a continuation-in-part application of U.S. patent application Ser. No. 12/108,144, filed Apr. 23, 2008, now U.S. Pat. No. 7,846,420, which claims benefit of priority to U.S. Provisional Patent Application Ser. No. 60/913,315, filed Apr. 23, 2007, the contents of which are incorporated herein by reference in their entireties.

BACKGROUND OF THE INVENTION

Johne's disease is a chronic diarrheal enteric disease in ruminants that is caused by *Mycobacterium avium* subspecies *paratuberculosis* (MAP)(Johne & Frothingham (1895) *Dtsch. Zeitschr. Tiermed. Vergl. Pathol.* 21:438-454). Live MAP is shed into the milk of cows with Johne's disease (Sweeney (1996) *Vet. Clin. North Am. Food Anim. Pract.* 12(2):305-12). MAP has been cultured from commercially available pasteurized milk in Europe and the United States (Grant (1998) *Appl. Environ. Microbiol.* 64(7):2760-1; Ellingson, et al. (2005) *J. Food Prot.* 68(5):966-72). When Crohn's disease was first described (Crohn, et al. (1932) *J. Amer. Med. Assoc.* 99:1323-1328), similarities to Johne's disease were identified (Dalziel (1913) *Br. Med. J.* ii:1068-1070). However, in humans MAP exists in the cell wall-deficient form (Chiodini (1987) *J. Clin. Microbiol.* 25:796-801). Therefore, in the early analysis of Crohn's disease, MAP could not be detected in humans by the mycobacterial identification techniques of the time, because such techniques stained the mycobacterial cell wall (Ziehl (1882) *Dtsch. Med. Wschr.* 8:451; Neelsen (1883) *Zbl. Med. Wiss.* 21:497-501). However, since 1913 the presence of MAP has been identified in humans by other means (see, e.g., Greenstein (2003) *Lancet Infect. Dis.* 3(8):507-14) and an infectious etiology has been posited for some (Hermon-Taylor (1998) *Ital. J. Gastroenterol. Hepatol.* 30(6):607-10; Borody, et al. (2002) *Dig. Liver Dis.* 34(1):29-38), or all (Greenstein (2005) Genetics, Barrier Function, Immunologic & Microbial Pathways. Munster, Germany:25) of inflammatory bowel disease (IBD).

Since the first detection of MAP RNA (Mishina, et al. (1996) *Proc. Natl. Acad. Sci. USA* 93(18):9816-9820), MAP has been suggested as being the primary and unique, etiological agent of all IBD (Naser, et al. (2004) *Lancet* 364(9439): 1039-1044; Autschbach, et al. (2005) *Gut* 54(7):944-9; Greenstein (2005) supra; Greenstein (2005) Genetics, Barrier Function, Immunologic & Microbial Pathways. Munster, Germany:24; Greenstein (2005) Crohn's and Colitis Foundation (CCFA) National Research and Clinical Conference. Fourth Annual Advances in Inflammatory Bowel Disease. Miami, Fla.:211) including Perforating and Non-perforating Crohn's disease (Greenstein, et al. (1988) *GUT* 29:588-592; Gilberts, et al. (1994) *Proc. Natl. Acad. Sci. USA* 91(126): 12721-12724) and ulcerative colitis. It is believed that the particular clinical presentation of IBD that manifests is dependent upon the infected individual's immune response to MAP (Gilberts, et al. (1994) supra). This is analogous to another mycobacterial disease, leprosy. There are two clinical forms of leprosy, tuberculoid and lepromatous (Hansen (1874) *Norsk Magazin Laegevidenskaben* 4:1-88), both of which are caused by the same organism, *M. leprae*. The form of leprosy that manifests in a given individual is determined by the immune response of the infected patient (Yamamura, et al. (1991) *Science* 254:277-279), not by the phenotype or genotype of the leprosy *bacillus*.

It has been suggested that Koch's postulates (Koch (1882) *Berl. Klin. Wschr.* 19:221-230), originally promulgated for use in demonstrating tuberculosis infection, may have been met for MAP in Crohn's disease (Greenstein (2003) supra) and more recently for MAP in ulcerative colitis (Greenstein (2005) supra; Naser, et al. (2004) supra).

The link between MAP infection and other diseases is under investigation. An association between ulcerative colitis and Multiple Sclerosis has been suggested (Rang, et al. (1982) *The Lancet* pg. 555) and the positive association between IBD incidence rates and Multiple Sclerosis has led to the suggestion that these two chronic, immunologically-mediated diseases may have a common environmental etiology (Green, et al. (2006) *Am. J. Epidemiol.* 164(7):615-23). However, the common causal agent of ulcerative colitis and Multiple Sclerosis was not identified. Moreover, while the symptoms of Multiple Sclerosis have been ameliorated with variety of therapeutic agents including azathioprine, methotrexate, cyclophosphamide and mitoxantrone (Kaffaroni, et al. (2006) *Neurol. Sci.* 27 Suppl. 1:S13-7), which have been suggested to mediate the secondary inflammatory response, there has been no indication that these agents affect the primary etiological agent.

There is increasingly compelling evidence that MAP may be zoonotic (Greenstein & Collins (2004) *Lancet* 364(9432): 396-7) and a human pathogen in gastrointestinal disease (Greenstein (2005) supra) and other diseases as well. There is an additional indication that in man, MAP is systemic and not confined to the gastrointestinal tract (Naser, et al. (2000) *Am. J. Gastroenterol.* 95(4):1094-5; Naser, et al. (2004) *Lancet* 364(9439):1039-1044). It is suggested that the reason MAP is zoonotic and has been missed as an etiological agent is that the medical profession has been unknowingly treating MAP with anti-inflammatory agents (e.g., 5-amino salicylic acid, methotrexate, and 6-mercaptopurine), which in fact have anti-MAP activity (Greenstein, et al. (2007) *PLoS ONE* 2:e161; Greenstein, et al. American Society of Microbiology 2007, Toronto, Canada). It is therefore of concern that viable MAP is found in the food chain (Eltholth, et al. (2009) *J. Appl. Microbiol.* 107:1061-1071), including pasteurized milk (Ellingson, et al. (2005) supra), and potable chlorinated municipal water (Mishina, et al. (1996) *Proc. Natl. Acad. Sci. USA* 93:9816-9820).

Accordingly, from the perspective of both animal and human health, control of Johne's disease is desirable. However, governmental agencies have been reluctant to initiate global Johne's disease vaccination programs over concern for the loss of ability to diagnose tuberculosis using skin testing.

SUMMARY OF THE INVENTION

The present invention is a method for producing a vaccine for immunizing a subject against mycobacterial infection by admixing (a) at least one *Mycobacterium avium* subspecies *paratuberculosis* (MAP) antigen, or attenuated or killed MAP; (b) at least one antigen isolated from a member of the *M. tuberculosis* complex (MTC), or an attenuated or killed *mycobacterium* from the MTC; and (c) a suitable carrier. In one embodiment, the attenuated or killed MAP is cell wall-competent or cell wall-deficient. In another embodiment, the MAP antigen is GroES, AhpD, 32 kDa antigen, kDa antigen, 34.5 kDa antigen, 35 kDa antigen, 36 kDa antigen, 42 kDa antigen, 44.3 kDa antigen, AhpC antigen or 65 kDa antigen. In a further embodiment, the member of the MTC is selected from the group of *M. tuberculosis, M. bovis, M. bovis* Calmette-Guérin, *M. africanum, M. canetti, M. caprae, M. pinnipedii* and *M. microti*.

Vaccines and methods for immunizing a subject against mycobacterial infection, preventing or treating mycobacterial infection, and preventing a disease associated with a mycobacterial infection in human and non-human subjects are also provided.

DETAILED DESCRIPTION OF THE INVENTION

Epidemiological analysis identifies a parallelism in the increasing incidence of Crohn's disease, ulcerative colitis and Multiple Sclerosis (Green, et al. (2006) supra). In Alzheimer's disease the use of "anti-inflammatories" shows therapeutic benefit (Rogers, et al. (1993) *Neurology* 43(8):1609-11). Additionally, there is the suggestion that rheumatoid arthritis is protective against Alzheimer's disease (McGeer, et al. (1990) *Lancet* 335(8696):1037). Analogous to lepromatous leprosy (Hansen (1874) *Norsk Magazin for Laegevidenskaben* 4:1-88) and tuberculoid leprosy, it is now posited that Multiple Sclerosis and perforating Crohn's disease (Gilberts, et al. (1994) *Proc. Natl. Acad. Sci. USA* 91(126):12721-12724) are the "acute" forms of a *Mycobacterium avium* subspecies *paratuberculosis* (MAP; basonym *M. paratuberculosis*) infection, whereas Alzheimer's Disease and obstructive Crohn's or ulcerative colitis are the chronic forms of a MAP infection. It is further posited that a causative relationship between MAP and diseases such as IBD and Multiple Sclerosis have been missed because it has not been appreciated that standard "immunomodulatory" treatment regimes, whose mechanisms of actions are unknown or speculated upon, are in fact effective because they are treating a MAP infection. It is posited that MAP is also responsible for a variety of diseases where an infectious etiology has been suggested, e.g., sarcoidosis, ankylosing spondylitis, psoriasis, and psoriatic arthritis and rheumatoid arthritis. Coincidentally, these diseases are often treated with "immunomodulatory" and "anti-inflammatory" agents that have now been shown to interfere with the growth kinetics of MAP.

While some reports have indicated that high-temperature short-time pasteurization does not effectively kill MAP in milk (Grant, et al. (1998) *Lett. Appl. Microbiol.* 26:166-170; Grant, et al. (1999) *Lett. Appl. Microbiol.* 28:461-465), killing by turbulent-flow conditions has been demonstrated (Stabel, et al. (1997) *Appl. Environ. Microbiol.* 63:4975-4977). Given the identification of potential sources of infection and that MAP is widespread over the industrialized as well as non-industrialized world and, a multipronged approach including vaccines, antibiotics, and public health measures are needed to control and prevent MAP infections as well as infections by one or more members of the *M. tuberculosis* complex (MTC). Accordingly, the present invention provides vaccines and methods for immunizing human and non-human subjects against mycobacterial infection.

As is known in the art, mycobacteria that cause human and/or animal tuberculosis (TB) are grouped together within the *Mycobacterium tuberculosis* complex. Members of the *M. tuberculosis* complex include *M. tuberculosis, M. bovis, M. bovis* Calmette-Guérin (BCG), *M. africanum, M. canetti, M. caprae, M. pinnipedii* and *M. microti* (Huard, et al. (2006) *J. Bacteriol.* 188:4271-4287). In one embodiment of the present invention, the instant vaccine and methods are used in the prevention and/or treatment of MAP and *M. tuberculosis* infection. In another embodiment, the instant vaccine and methods are used in the prevention and/or treatment of MAP and *M. bovis* infection. In yet a further embodiment, the instant vaccine and methods are used in the prevention and/or treatment of MAP, *M. tuberculosis* and *M. bovis* infection.

For the purposes of the present invention, a vaccine is intended to include whole cells, which in the case of MAP can be either cell wall-competent or cell wall-deficient; cell extracts; isolated protein (i.e., a subunit vaccine); or combinations thereof. Whole cell vaccines can be produced from mycobacteria that have been attenuated or have been killed. Attenuated means that the microorganisms are treated to reduce virulence, but maintain viability. Mycobacteria can be attenuated using any conventional strategy. For example, serial passage or long-term maintenance of the organism in culture media can be employed to attenuate mycobacteria. Live attenuated vaccines have the advantage of mimicking the natural infection enough to trigger an immune response similar to the response to the wild-type organism. Such vaccines generally provide a high level of protection, especially if administered by a natural route, and some may only require one dose to confer immunity. In the case of MAP, which exists in humans in the cell wall-deficient state, a vaccine that targets this obligate intracellular form is desirable. By way of illustration, cell wall-competent and cell wall-deficient (i.e., spheroplasts) vaccine preparations have been shown to reduce lesion scores associated with Johne's Disease in baby goats (Hines, et al. (2005) 8$^{th}$ *International Colloquium on Paratuberculosis*, Copenhagen, Denmark). Attenuated *M. tuberculosis* strains are described, for example, in U.S. Pat. No. 7,722,861, wherein stains are genetically engineered to be auxotrophic for a vitamin.

In contrast to an attenuated vaccine, a vaccine containing killed mycobacteria means that the microorganisms are no longer viable, but are still capable of eliciting an immune response in the target animal. Mycobacteria can be killed using a number of different agents including, but not limited to, formalin, azide, freeze-thaw, sonication, heat treatment, sudden pressure drop, detergent (especially non-ionic detergents), lysozyme, phenol, proteolytic enzymes, propiolactone, Thimerosal (see, U.S. Pat. No. 5,338,543), and binary ethyleneimine (see, U.S. Pat. No. 5,565,205). By way of illustration, vaccination of calves with a heat-killed field strain of MAP results in high concentrations of IFN-γ and better protection against a MAP challenge exposure than does a commercially available vaccine (Uzonna, et al. (2002) *Proc. 7$^{th}$ Intl. Coll. Paratuberculosis*; Juste (ed)).

In addition, or as an alternative to a vaccine containing attenuated or killed mycobacteria, a subunit vaccine can be employed. Any known mycobacterial antigen, or antigen fragment thereof, commonly employed in veterinary medicine can be used in the vaccine and methods of the present invention.

Examples of suitable MAP antigens include, but are not limited to, the antigens listed in Table 1.

TABLE 1

| MAP protein | Characteristic | Size (kDa) | SEQ ID NO: |
|---|---|---|---|
| GroES | Heat shock protein | 10 | 1 |
| AhpD | Alkyl hydroperoxide reductase D | 19 | 2 |
| 32-kDa antigen | Fibronectin binding properties, secreted | 32 | |
| 34-kDa antigen | Cell wall antigen, B-cell epitope | 34 | 3 |
| 34-kDa antigen | Serine protease | 34 | 4 |
| 34.5-kDa antigen | Cytoplasmic protein | 34.5 | |
| 35-kDa antigen | Immunodominant protein | 35 | |
| 36-kDa antigen | p36 antigen | 36 | 5 |
| 42-kDa antigen | Cytoplasmic protein | 42 | |
| 44.3-kDa antigen | Soluble protein | 44.3 | |

TABLE 1-continued

| MAP protein | Characteristic | Size (kDa) | SEQ ID NO: |
|---|---|---|---|
| AhpC | Alkyl hydroperoxide reductase C | 45 | 6 |
| 65-kDa antigen | GroEL heat shock protein | 65 | 7 |

The 32-kDa secreted protein with fibronectin binding properties has been implicated in protective immunity (Andersen, et al. (1991) Infect. Immun. 59:1905-1910; El-Zaatari, et al. (1994) Curr. Microbiol. 29:177-184) and the 34-kDa cell wall antigenic protein is homologous to a similar immunogenic protein in M. leprae (De Kesel, et al. (1992) Scand. J. Immunol. 36:201-212; De Kesel, et al. (1993) J. Clin. Microbiol. 31:947-954; Gilot, et al. (1993) J. Bacteriol. 175:4930-4935; Silbaq, et al. (1998) Infect. Immun. 66:5576-5579). The seroreactive 34-kDa serine protease expressed in vivo by MAP has also been described (Cameron, et al. (1994) Microbiology 140:1977-1982; however, this antigen is different from the 34-kDa antigen described above. Another strongly immunoreactive protein of kDa has also been identified in M. avium complex isolates, including MAP (El-Zaatari, et al. (1997) J. Clin. Microbiol. 35:1794-1799). A more thoroughly characterized protein of 65 kDa from MAP is a member of the GroEL family of heat shock proteins (El-Zaatari, et al. (1994) Curr. Microbiol. 29:177-184; El-Zaatari, et al. (1995) Clin. Diagn. Lab. Immunol. 2:657-664). Like the GroES proteins, the GroEL antigens from other mycobacteria are highly immunogenic (Shinnick (1987) J. Bacteriol. 169:1080-1088; Thole, et al. (1987) Infect. Immun. 55:1466-1475; Thole, et al. (1988) Infect. Immun. 56:1633-1640).

The alkyl hydroperoxide reductases C and D (AhpC and AhpD) have also been characterized as immunogenic proteins of MAP (Olsen, et al. (2000) Infect. Immun. 68:801-808). Unlike other mycobacteria, large amounts of these antigens are produced by MAP when the bacilli are grown without exposure to oxidative stress. AhpC is the larger of the two proteins and appears to exist as a homodimer in its native form since it migrates at both 45 and 24 kDa under denaturing conditions. In contrast, AhpD is a smaller monomer, with a molecular mass of about 19 kDa. Antiserum from rabbits immunized against AhpC and AhpD reacted only with MAP proteins and not with proteins from other mycobacterial species, indicating that antibodies against these proteins are not cross-reactive. Furthermore, peripheral blood monocytes from goats experimentally infected with MAP were capable of inducing gamma interferon (IFN-γ) responses after stimulation with AhpC and AhpD, confirming their immunogenicity (Olsen, et al. (2000) Infect. Immun. 68:801-808).

Antigenic proteins of M. tuberculosis are known in the art and include but are not limited to, PirG protein encoded by the Mtb gene Rv3810; PE-PGRS protein encoded by the Mtb gene Rv3367; PTRP protein encoded by the Mtb gene Rv0538; MtrA protein encoded by the Mtb gene Rv3246c; MTb81, Mo2, FL TbH4, HTCC#1 (Mtb40), TbH9, MTCC#2 (Mtb41), DPEP, DPPD, TbRa35, TbRa12, MTb59, MTb82, Erd14 (Mtb16), DPV (Mtb8.4), MSL (Mtb9.8), MTI (Mtb9.9A, also known as MTI-A), Ag85B, ESAT-6, and α-crystalline antigens of M. tuberculosis. In some embodiments, the antigenic protein provides cross-protection against M. tuberculosis and M. bovis, i.e., antibodies to said protein recognize the protein from both M. tuberculosis and M. bovis. In other embodiments, the antigenic protein is specific for M. tuberculosis and absent from the genome of BCG. Examples of such antigens include M. tuberculosis BCG Negative polypeptides, MTBN1-MTBN8. These and other antigens are described, for example, in U.S. Pat. Nos. 7,745,141; 7,579,141; and 7,311,922, incorporated herein by reference.

Antigenic proteins of M. bovis are also known in the art. For example, U.S. Pat. No. 7,670,609 describes a recombinant Bacille Calmette-Guerin (BCG) subunit-based vaccine.

Antigenic proteins disclosed herein, can be prepared and isolated by any conventional method including recombinant production. The term isolated does not require absolute purity; rather, it is intended as a relative definition, and can include preparations that are highly purified or preparations that are only partially purified. When recombinantly produced, antigenic proteins of the invention can also be produced as fusion proteins containing more than one antigen (e.g., fusion of antigen 85B (Ag85B) and ESAT-6) or fusion proteins containing an antigen in combination with an adjuvant or carrier protein.

It is contemplated that various combinations of antigen proteins, and/or attenuated and/or killed mycobacteria can be employed. By way of illustration, a vaccine of the invention can be composed of heat-killed MAP in combination with attenuated BCG. As another example, a vaccine of the invention can include an antigenic protein from MAP in combination with attenuated BCG and proteins Ag85B and ESAT-6 from M. tuberculosis.

Vaccines of the present invention are prepared using routine methods. Generally, vaccines are prepared as injectables, in the form of aqueous solutions or suspensions. Vaccines in an oil base are also well-known such as for inhalation. Solid forms which are dissolved or suspended prior to use can also be formulated. Suitable carriers, diluents and excipients are generally added that are compatible with the active ingredients and acceptable for use in humans and non-human animals. Examples of such carriers include, but are not limited to, water, saline solutions, dextrose, or glycerol. Carriers can also include liposomes or microspheres. Combinations of carriers can also be used. For example, prime immunization with BCG and a subunit vaccine (proteins Ag85B and ESAT-6) in liposomes followed by boosting with the subunit vaccine in conventional adjuvant has been shown to result in an increase in the protective efficacy of up to 7-fold compared with BCG alone and 3-fold compared with unaugmented BCG boosted by subunit vaccine (Dietrich, et al. (2007) J. Immunol. 178:7321-3730). A generally recognized compendium of methods and ingredients of vaccine compositions is Remington: The Science and Practice of Pharmacy, Alfonso R. Gennaro, editor, 20th ed. Lippincott Williams & Wilkins: Philadelphia, Pa., 2000.

Vaccine compositions can further incorporate additional substances to stabilize pH, or to function as adjuvants, wetting agents, or emulsifying agents, which can serve to improve the effectiveness of the vaccine. Examples of suitable adjuvants include, but are not limited to, aluminum salts; Incomplete Freund's adjuvant; threonyl and n-butyl derivatives of muramyl dipeptide; lipophilic derivatives of muramyl tripeptide; monophosphoryl lipid A; 3'-de-O-acetylated monophosphoryl lipid A; cholera toxin; QS21; phosphorothionated oligodeoxynucleotides with CpG motifs and adjuvants disclosed in U.S. Pat. No. 6,558,670.

Vaccines are generally formulated for parenteral administration and are injected either subcutaneously or intramuscularly. Vaccines can also be formulated as suppositories or for oral or nasal administration using methods known in the art. For example, The amount of vaccine sufficient to confer immunity to pathogenic mycobacteria is determined by methods well-known to those skilled in the art. This quantity will be determined based upon the characteristics of the vaccine recipient and the level of immunity required. Typically, the amount of vaccine to be administered will be determined based upon the judgment of a skilled physician or veterinarian. Where vaccines are administered by subcutaneous or intramuscular injection, a range of 0.5 to 500 µg purified protein can be given.

The present invention is also directed to a vaccine in which an antigenic protein, or antigenic fragment thereof, is delivered or administered in the form of a polynucleotide encoding the protein or fragment (i.e., a DNA vaccine). In DNA vaccination, the subject is administered a polynucleotide encoding a antigenic protein that is then transcribed, translated and expressed in some form to produce strong, long-lived humoral and cell-mediated immune responses to the antigen. The polynucleotide can be administered using viral vectors or other vectors, such as liposomes, and can be combined with an acceptable carrier.

In addition, the proteins of the present invention can be used as antigens to stimulate the production of antibodies for use in passive immunotherapy, for use as diagnostic reagents, and for use as reagents in other processes such as affinity chromatography.

The present invention also embraces a method of using the instant vaccine as a means of immunizing animals, including humans and non-human animals such as sheep and cattle, against mycobacterial infection. In accordance with such a method, a vaccine containing mycobacterial antigens and/or attenuated and/or killed mycobacteria is administered to a subject in an amount effective to stimulate a measurable immune response. A measurable immune response can include a humoral response (e.g., production of antibodies to a particular antigen) or cell-mediate immune response (e.g., elicitation of a T cell response as determined by the production of cytokines such as IFN-gamma or IL-10).

In so far as the vaccine disclosed herein can be used to immunize a subject against mycobacterial infection, the present invention also provides for a method of preventing or treating mycobacterial infection, as well as a disease associated with mycobacterial infection. Such methods involve administering to a subject (humans and non-human animals) a vaccine containing at least one mycobacterial antigens and/or attenuated and/or killed mycobacteria, as disclosed herein, in an amount effective to prevent or attenuate said mycobacterial infection or symptoms of the mycobacterial-associated disease. In using the methods of the invention, the disease to be prevented or treated is desirably ulcerative colitis, irritable bowel syndrome, Crohn's Disease, Multiple Sclerosis, Alzheimer's Disease, sarcoidosis, ankylosing spondylitis, psoriasis, psoriatic arthritis rheumatoid arthritis, tuberculosis, and/or Johne's disease.

The invention is described in greater detail by the following non-limiting examples.

EXAMPLE 1

Prevalence of Johne's Disease in Vaccinated and Unvaccinated Ovine

Methods.

Data on the number of Ovine Johne's Disease (OJD) infected herds detected in New South Wales (NSW), Australia from 1980 to December 1998 were obtained. Positive herds were identified by both on-farm testing and confirmatory histopathology.

In 20 abattoirs in NSW, from November 1999 to December 2009, all consignments of sheep ≧2 years of age sent for slaughter were examined for the presence of OJD using methods known in the art (Bradley & Cannon (2005) Aust. Vet. J. 83:633-636). In brief, trained inspectors visually and by palpation examined the terminal ileum and adjacent lymph nodes of the animals. Positive tissues were then further examined histopathologically using Ziehl (Ziehl (1882) Dtsch. Med. Wschr. 8:451)-Neelsen (Neelsen (1883) Zbl. Med. Wiss. 21) staining. This method has a 74-87% individual animal sensitivity, and a 97-98% specificity (Bradley & Cannon (2005) supra). The higher values were found in areas designated as "High prevalence" (Bradley & Cannon (2005) supra).

Data collected by the inspectors included: the name and location of the Abattoir; date killed; consignment reference (Lot number); the total number of animals inspected; the number or estimated percentage of lesions grossly resembling OJD; the area of origin of the sheep and/or the property identification code (where available), which defines the Local Government Area and the property locality; the age (minimum 2 years or older); and sex of the animals.

OJD Prevalence Regions ("High", "Medium" and "Low") have been established by the NSW Department of Primary Industries. A maximum of three samples per consignment were submitted for histopathology. During the course of this study there was an evolution in the tissues examined. Initially multiple sites were examined and sampled (terminal ileum, ileo-caecal valve and associated lymph nodes.) Subsequently, only the terminal ileum was examined because of the large number of animals involved and minimal loss of sensitivity.

Consignments were initially classified on the basis of histopathology as positive (P), negative (N) or inconclusive (I). Samples were declared as Inconclusive when no Ziehl-Neelsen acid-fast organisms were detected despite the presence of granulomas typical of OJD. Consignments identified as "Inconclusive" were removed from the dataset with the following exception. When a consignment included inconclusive histopathology, these were attributed to OJD if other lesions from the same consignment were Ziehl-Neelsen positive or if OJD had been confirmed in the flock within the prior 2 years. Such flocks are designated as "Inconclusive Positive" (IP). P and IP are analyzed as Positive for the purpose of this report.

To account for other causes of intestinal abnormalities (e.g. coccidiosis, parasitism, salmonellosis, bacterial enteritis, etc.) the calculated number of lesions in positive lines were corrected pro-rata according to the number of lesions that were negative versus positive on histopathology.

Data for the units of GUDAIR® vaccine used were obtained from the Veterinary Authorities in NSW and sales data provided by the distributors CSL (Victoria, Australia) and Pfizer Australia.

Results.

There was a progressive increase in the incidence of OJD starting in 1980 in NSW with acceleration in the incidence over the next two decades. By 1998, 204 flocks were newly diagnosed with OJD, when the cumulative total of infected flocks was 441. Within Australia, the highest prevalence of OJD was in New South Wales and Victoria.

From 1999 to 2009, there were 33,735 total consignments of sheep sent to abattoirs, of which 40% (13,569) were from the High Prevalence Region (Table 2). A total of 7,807,937 carcasses were inspected, of which 39% (3,031,531) were from the High Prevalence region (Table 3). OJD was identified in 13% (4,454 (Table 4)/33,735 (Table 2)) of all consignments, of which 95% (4222/4454; Table 4) were from the High prevalence region. Within the High Prevalence region itself, 31% of consignments (4,222 (Table 4)/13,569 (Table 2)) were positive for OJD. A total of 1,212,859 carcasses were inspected in the positive consignments, of which 95% (1,150, 196/1,212,859 (Table 5)) were from the High Prevalence region. Using established criteria, 46,259 animals had OJD, of which 96% (44,374/46,259 (Table 6)) were from the High Prevalence region. Within the High Prevalence region, an average of 3.8% (44,374 (Table 6)/1,150,196 (Table 5)) of carcasses had OJD lesions.

TABLE 2

| Year | High | Medium | Low | Total/yr. |
|---|---|---|---|---|
| 1999 | 150 | 12 | 68 | 231 |
| 2000 | 2171 | 294 | 2400 | 4991 |
| 2001 | 1656 | 208 | 1979 | 4043 |
| 2002 | 1879 | 163 | 1751 | 3917 |
| 2003 | 986 | 139 | 1084 | 2303 |
| 2004 | 1204 | 105 | 1340 | 2670 |
| 2005 | 747 | 89 | 1224 | 2065 |
| 2006 | 1640 | 132 | 2006 | 3785 |
| 2007 | 1276 | 235 | 2316 | 3829 |
| 2008 | 1025 | 167 | 2004 | 3196 |
| 2009 | 835 | 54 | 1816 | 2705 |
| Total 1999-2009 | 13569 | 1598 | 17988 | 33735 |

The numbers of consignments from 1999-2009 stratified by region of OJD prevalence region and with the total of the three regions.

TABLE 3

| Year | High | Medium | Low | Total/Yr |
|---|---|---|---|---|
| 1999 | 33,102 | 3,224 | 20,163 | 56,489 |
| 2000 | 442,298 | 42,807 | 614,223 | 1,099,328 |
| 2001 | 350,731 | 28,443 | 511,640 | 890,814 |
| 2002 | 398,049 | 28,725 | 421,616 | 848,390 |
| 2003 | 191,606 | 25,097 | 220,764 | 437,467 |
| 2004 | 258,536 | 23,817 | 300,429 | 582,782 |
| 2005 | 164,839 | 20,677 | 300,093 | 485,609 |
| 2006 | 461,572 | 31,334 | 507,132 | 1,000,038 |
| 2007 | 292,935 | 57,749 | 576,465 | 927,149 |
| 2008 | 243,764 | 39,124 | 507,008 | 789,896 |
| 2009 | 194,099 | 11,536 | 484,340 | 689,975 |
| Total 11 years | 3,031,531 | 312,533 | 4,463,873 | 7,807,937 |

The numbers of carcasses inspected from 1999-2009 stratified by New South Wales Prevalence Region of OJD. Total per year (right hand column) and Cumulative Total per Prevalence Region from 1999-2009 (bottom row) are included.

TABLE 4

| Year | High | Medium | Low | (+)/Year |
|---|---|---|---|---|
| 1999 | 41 | 2 | 1 | 44 |
| 2000 | 421 | 6 | 10 | 438 |
| 2001 | 471 | 11 | 13 | 496 |
| 2002 | 667 | 11 | 8 | 689 |
| 2003 | 330 | 12 | 3 | 346 |
| 2004 | 395 | 17 | 6 | 418 |
| 2005 | 189 | 4 | 10 | 203 |
| 2006 | 634 | 8 | 14 | 656 |
| 2007 | 480 | 20 | 16 | 516 |
| 2008 | 346 | 20 | 16 | 382 |
| 2009 | 248 | 10 | 8 | 266 |
| Total (+) 11 Years | 4222 | 121 | 105 | 4454 |

The numbers of consignments where OJD was detected from 1999-2009 stratified by New South Wales Prevalence Region. Total per year (right hand column) and Cumulative Total per Prevalence Region from 1999-2009 (bottom row) are included.

TABLE 5

| Year | High | Medium | Low | Total/Yr |
|---|---|---|---|---|
| 1999 | 11,893 | 495 | 288 | 12,676 |
| 2000 | 104,047 | 902 | 4,618 | 109,567 |
| 2001 | 106,992 | 2,740 | 3,600 | 113,332 |
| 2002 | 153,454 | 1,997 | 2,491 | 157,942 |
| 2003 | 77,920 | 2,879 | 1,455 | 82,254 |
| 2004 | 100,276 | 4,285 | 1,896 | 106,457 |
| 2005 | 60,667 | 1,300 | 2,212 | 64,179 |
| 2006 | 221,343 | 1,728 | 4,315 | 227,386 |
| 2007 | 141,561 | 6,366 | 4,141 | 152,068 |
| 2008 | 98,344 | 4,634 | 5,965 | 108,943 |
| 2009 | 73,699 | 2,449 | 1,907 | 78,055 |
| Grand Total | 1,150,196 | 29,775 | 32,888 | 1,212,859 |

The numbers of sheep inspected in consignments where OJD was detected from 1999-2009 stratified by New South Wales Prevalence Region. Total per year (right hand column) and Cumulative Total per Prevalence Region from 1999-2009 (bottom row) are included.

TABLE 6

| Year | High | Medium | Low | Total/yr |
|---|---|---|---|---|
| 1999 | 1145 | 26 | 1 | 1,172 |
| 2000 | 9789 | 132 | 75 | 9,996 |
| 2001 | 5914 | 213 | 72 | 6,199 |
| 2002 | 8794 | 23 | 22 | 8,839 |
| 2003 | 3805 | 205 | 181 | 4,190 |
| 2004 | 4025 | 214 | 14 | 4,253 |
| 2005 | 1437 | 15 | 57 | 1,509 |
| 2006 | 3530 | 20 | 26 | 3,576 |
| 2007 | 2445 | 88 | 41 | 2,574 |
| 2008 | 2039 | 168 | 94 | 2,302 |
| 2009 | 1449 | 139 | 59 | 1,647 |
| Total in 11 years | 44374 | 1243 | 642 | 46,259 |

The numbers of sheep in positive consignments where OJD lesions were detected from 1999-2009 stratified by New South Wales Prevalence Region. Total per year (right hand column) and Cumulative Total per Prevalence Region from 1999-2009 (bottom row) are included.

Initially, vaccination in NSW began in late 1999 in a major trial (Reddacliff, et al. (2006) *Vet. Microbiol.* 115:77-90). From 2000-2002, by special permit limited to 50 flocks (total 155,523 sheep), vaccination was offered to owners of heavily infected flocks that had previously suffered a minimum of 5% annual mortality consequent to OJD. In April 2002, OJD vaccination was approved and registered for Australia. Administration began more widely on a voluntary basis. By 2009, a total of 10.7 million doses had been administered, of which 93% (9.8 million) were administered in the region of High Prevalence (Table 7). In the High Prevalence Region, the maximal number of vaccinations administered was in 2003, 1.7 million (Table 7). There has been a gradual, and erratic, decline in the number of yearly doses administered falling to 0.96 million doses in the High Prevalence region by 2009 (Table 7). In contrast, there has been a progressive increase, albeit at a far lower number, in the number of vaccinations administered in the region of Medium Prevalence rising 88% (from 50 to 94 thousand) from 2003 to 2009 (Table 7).

TABLE 7

| Year | High | Medium | Low | All |
|---|---|---|---|---|
| 1999 | — | — | — | — |
| 2000 | — | — | — | — |
| 2001 | 398,399 | 7,488 | 5,214 | 411,100 |
| 2002 | 943,057 | 17,443 | 609 | 961,109 |
| 2003 | 1,656,569 | 49,509 | 11,796 | 1,717,873 |
| 2004 | 1,553,554 | 69,891 | 45,916 | 1,669,360 |
| 2005 | 1,545,161 | 65,117 | 50,073 | 1,660,350 |
| 2006 | 1,191,433 | 67,198 | 44,818 | 1,303,449 |
| 2007 | 538,850 | 55,450 | 10,450 | 604,750 |
| 2008 | 1,002,650 | 94,100 | 35,150 | 1,131,900 |
| 2009 | 955,450 | 94,700 | 49,800 | 1,099,950 |
| Total 2001/9 | 9,953,073 | 533,894 | 258,975 | 10,745,941 |

The numbers of vaccinations sold in New South Wales stratified by OJD Prevalence Region. Total per year (right hand column) and Cumulative Total per Prevalence Region from 1999-2009 (bottom row) are included. No Vaccinations were performed in 1999 or 2000.

During the course of the study the percentage of consignments that were positive remained erratically constant (High Prevalence Region: 27% in 1999 to 30% in 2009; Table 4) In noteworthy contrast, the % of animals that were positive for OJD in the High Prevalence Region fell progressively (High Prevalence Region 3.5% in 1999 to 0.75% 2009). In contrast, a countervailing trend was seen in the Medium Prevalence Region. Toward the end of the study, albeit with far fewer numbers, starting in 2005, there was an increase in the % positive consignments (Table 4). The number of animals positive as a % of the total number of animals inspected, increased from 0.06% in 2006 to 1.2% in 2009 (Table 6).

It was subsequently determined whether there was an association between the use of vaccination and trends in the incidence of OJD. From the time of institution of vaccination, there was a progressive decrease in the % lesions (+) per consignment (+). A more detailed analysis showed that fewer animals/consignment were infected as vaccination proceeded. The decrease was most pronounced when >10% of lesions were positive in a positive consignment (16% in 2001 falling to 4% by 2009. In contrast, there was a progressive increase in fewer animals per consignment being infected as vaccination proceeded (e.g. <1% of animals infected/infected consignment=24% in 2001 rising to 48% by 2009.

Conclusion:

Controlling Johne's Disease is important for the agricultural industry and veterinary community. Despite pilot studies showing Johne's Disease control with herd, animal and stool management (Collins, et al. (2010) *J. Dairy Sci.* 93:1638-1643), the increasing prevalence of Johne's Disease in cattle remains an obvious cause for concern.

The data herein show that prior to the initiation of vaccination, particularly in the High Prevalence areas, OJD in NSW was increasing. Following the institution of OJD vaccination program, a region-wide decrease in the prevalence and incidence of OJD is observed. It should however be noted that there are no similar encouraging results of a decrease in bovine Johne's Disease in the same geographical region during the same period.

The decrease in Johne's Disease in the High Prevalence Region was not replicated in the Medium Prevalence Region. These data may indicate that the Medium region may transitioning to a High Prevalence status.

Governmental agencies have been reluctant to initiate global Johne's Disease vaccination programs. The most compelling concern is the loss of ability to diagnose tuberculosis using skin testing. However, standard pasteurization of animal products satisfactorily kills *M. bovis* and *M. tuberculosis*. In contrast, MAP is not reproducibly killed by standard pasteurization. Therefore, a combination vaccine would be of use in addressing these problems.

EXAMPLE 2

Anti-Mycobacterial Vaccine

Mice (10 per group), e.g., wild-type and/or IL-18 deficient mice (Momotani, et al. (2002) *Proc. 7th Intl. Coll. Paratuberculosis*, Juste (ed)) are immunized intraperitoneally (i.p.) with either AhpC or AhpD protein (15 μg in 50 μl PBS (phosphate-buffered saline) in combination with an Ag85B-ESAT-6 fusion protein (15 μg in 50 μl PBS) emulsified in 50 μl complete Freund's adjuvant (CFA)). A group of 10 mice are sham-immunized with PBS and CFA only.

A second immunization of 15 μg of each antigen with incomplete Freund's adjuvant (IFA) is administered 3 weeks later (with the sham-immunized group receiving PBS and IFA).

Blood is drawn at weeks 5 and 7. Sera from each group are pooled for analysis of antigen-specific antibody production by ELISA. Mice are challenged at week 8 by intraperitoneal injection of MAP and *M. tuberculosis*. Mice are monitored for signs and symptoms of disease.

Data will indicate that immunization of mice with either recombinant AhpC or AhpD proteins in combination with the Ag85B-ESAT-6 fusion protein elicits a response capable of protecting against MAP and *M. tuberculosis* infection.

EXAMPLE 3

Immunogenicity of Anti-Mycobacterial Vaccine in Humans

Sera from patients with culture-proven MAP infection are used in western blot analysis containing recombinant AhpC or AhpD protein.

The results of this analysis will demonstrate that sera from patients with MAP infections exhibit reactivity with either AhpC or AhpD, thereby indicating that AhpC and AhpD are recognized by the human immune system and suggest that antibodies able to bind the AhpC or AhpD protein can be produced during natural MAP infection in humans. Further, this data provides evidence that AhpC and AhpD are expressed in vivo by MAP during infection, and thus can be available as targets for immunoprophylaxis, immunotherapy, or to provide immune responses in subjects vaccinated with these proteins.

What is claimed is:

1. A method for producing a vaccine for immunizing a subject against *Mycobacterium avium* subspecies *paratuberculosis* (MAP) and *M. tuberculosis* (MTB) infection comprising admixing
   (a) at least one isolated and purified MAP antigen, or attenuated or killed MAP, wherein the MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, 65 kDa antigen or AhpC antigen and the attenuated or killed MAP is cell wall-competent or cell wall-deficient;
   (b) at least one MTB antigen, or an attenuated or killed MTB; and
   (c) a suitable carrier
   thereby producing a vaccine for the immunization against MAP and MTB infection.

2. A method for immunizing a subject against *Mycobacterium avium* subspecies *paratuberculosis* (MAP) and *M. tuberculosis* (MTB) infection comprising administering to a subject a vaccine containing
   (a) at least one isolated and purified MAP antigen, or attenuated or killed MAP, wherein the MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, 65 kDa antigen or AhpC antigen and the attenuated or killed MAP is cell wall-competent or cell wall-deficient; and
   (b) at least one MTB antigen, or an attenuated or killed MTB,
   thereby immunizing the subject against MAP and MTB infection.

3. A method for treating *Mycobacterium avium* subspecies *paratuberculosis* (MAP) and *M. tuberculosis* (MTB) infection comprising administering to a subject a vaccine containing
   (a) at least one isolated and purified MAP antigen, or attenuated or killed MAP; and
   (b) at least one MTB antigen, or an attenuated or killed MTB,
   thereby treating MAP and MTB infection.

4. The method of claim 3, wherein the attenuated or killed MAP is cell wall-competent or cell wall-deficient.

5. The method of claim 3, wherein the MAP antigen is GroES, AhpD, 32 kDa antigen, kDa antigen, 34.5 kDa antigen, 35 kDa antigen, 36 kDa antigen, 42 kDa antigen, 44.3 kDa antigen, 65 kDa antigen or AhpC antigen.

6. The method of claim 3, wherein the subject is a non-human animal.

7. A method for preventing a disease associated with *Mycobacterium avium* subspecies *paratuberculosis* (MAP) and *M. tuberculosis* (MTB) infection comprising administering to a subject a vaccine containing
(a) at least one attenuated or killed MAP, wherein the attenuated or killed MAP is cell wall-competent or cell wall-deficient;
(b) at least one MTB antigen, or an attenuated or killed MTB,
thereby preventing a disease associated with MAP and MTB infection.

8. A method for preventing a disease associated with *Mycobacterium avium* subspecies *paratuberculosis* (MAP) and *M. tuberculosis* (MTB) infection comprising administering to a subject a vaccine containing
(a) at least one isolated and purified MAP antigen, wherein the MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, 65 kDa antigen or AhpC antigen;
(b) at least one MTB antigen, or an attenuated or killed MTB,
thereby preventing a disease associated with MAP and MTB infection.

9. A vaccine comprising
(a) at least one isolated and purified *Mycobacterium avium* subspecies *paratuberculosis* (MAP) antigen, or attenuated or killed MAP, wherein the MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, 65 kDa antigen or AhpC antigen and the attenuated or killed MAP is cell wall-competent or cell wall-deficient;
(b) at least one isolated and purified antigen from a member of the *M. tuberculosis* complex (MTC), or an attenuated or killed mycobacterium from the MTC; and
(c) a suitable carrier.

10. A vaccine consisting of:
(a) at least one attenuated or killed *Mycobacterium avium* subspecies *paratuberculosis* (MAP), wherein the attenuated or killed MAP is cell wall-competent or cell wall-deficient;
(b) at least one isolated and purified antigen from a member of the *M. tuberculosis* complex (MTC), or an attenuated or killed mycobacterium from the MTC; and
(c) a suitable carrier.

11. A vaccine consisting of:
(a) at least one *Mycobacterium avium* subspecies *paratuberculosis* (MAP) antigen, wherein the MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, 65 kDa antigen or AhpC antigen;
(b) at least one isolated and purified antigen from a member of the *M. tuberculosis* complex (MTC), or an attenuated or killed mycobacterium from the MTC; and
(c) a suitable carrier.

\* \* \* \* \*

UNITED STATES PATENT AND TRADEMARK OFFICE
CERTIFICATE OF CORRECTION

PATENT NO. : 8,465,753 B2
APPLICATION NO. : 12/956064
DATED : June 18, 2013
INVENTOR(S) : Robert J. Greenstein Page 1 of 1

It is certified that error appears in the above-identified patent and that said Letters Patent is hereby corrected as shown below:

In the Claims:

In Column 24, line 65, Claim 5, please delete "32 kDa antigen, kDa antigen,"
In Column 24, line 65, Claim 5, please insert --32 kDa antigen, 34 kDa antigen--

Signed and Sealed this
Seventeenth Day of September, 2013

Teresa Stanek Rea
*Deputy Director of the United States Patent and Trademark Office*